(12) United States Patent
Veeger et al.

(10) Patent No.: US 6,471,983 B1
(45) Date of Patent: Oct. 29, 2002

(54) SKIN APPLICATION AGENTS

(75) Inventors: Marcel Veeger, Goch (DE); Andreas Klotz, Grevenbroicher (DE); Bernd Nauels, Kempen (DE)

(73) Assignee: Stockhausen GmbH & Co. KG, Krefeld (DE)

( * ) Notice: Subject to any disclaimer, the term of this patent is extended or adjusted under 35 U.S.C. 154(b) by 0 days.

(21) Appl. No.: 09/666,466

(22) Filed: Sep. 20, 2000

(30) Foreign Application Priority Data

Aug. 18, 2000 (DE) .......................... 100 40 873

(51) Int. Cl.⁷ .............................. A61F 13/00; A61K 9/70
(52) U.S. Cl. .......................... 424/443; 42/400; 42/402; 42/484; 42/485; 42/489; 514/772.4
(58) Field of Search ................................ 424/402, 489, 424/443; 514/412, 772.4, 484, 400, 485

(56) References Cited

U.S. PATENT DOCUMENTS 5,580,942 A * 12/1996 Cornish ..................... 528/1
6,048,886 A * 4/2000 Neigut ..................... 514/412

FOREIGN PATENT DOCUMENTS

| EP | 0211183 A2 * | 2/1987 | .......... A61K/31/12 |
| EP | 0 535 789 | 4/1993 | |
| WO | WO 00/17300 | 3/2000 | |

OTHER PUBLICATIONS

Kraton Product sheets, Mar. 1999.*

* cited by examiner

Primary Examiner—Thurman K. Page
Assistant Examiner—Robert M. Joynes
(74) Attorney, Agent, or Firm—Oblon, Spivak, McClelland, Maier & Neustadt, P.C.

(57) ABSTRACT

The present invention relates to a skin application agent containing a polyisoprene latex.

33 Claims, No Drawings

SKIN APPLICATION AGENTS

The present invention relates to a skin application agent containing a polyisoprene latex.

Skin application agents, e.g. face masks, plasters and washing pastes, which often contain polymer latices, have been well-known for many years. However, the frequent disadvantage of these skin application agents is that they irritate the skin and are not toxicologically safe.

WO 00/17300 teaches a skin cleansing agent, which consists of a latex emulsion, an organosilicone compound, emollients, surface-active agents and water. The latex emulsion preferably has a styrene-butadiene copolymer.

The disadvantage of the above-mentioned skin cleansing agents is that they only have limited skin compatibility, are not toxicologically safe and/or pose environmental risks.

Well-known from EP 0,535,789 A2 is a cleansing composition for tropical applications, which contains a mixture of a surface-active agent, an emollient, a cationic material, a film former, a polyaminosugar condensate and water.

The object is therefore to provide a skin application agent which is toxicologically safe and causes similar or less skin irritation compared to the skin application agents of the prior art.

According to the invention, said object is accomplished by a skin application agent which contains a polyisoprene latex.

According to the invention, the skin application agent has a polyisoprene latex. This polyisoprene latex preferably has a content of at least 90% by weight cis-1,4-isoprene. The size of the polyisoprene particles in the latex is equally preferably 1.8 µm maximum. Furthermore, the latex has a solids content of preferably 20 to 90% by weight and especially preferably 60 to 80% by weight.

In a preferred embodiment, the skin application agent is a cosmetic and/or medical skin application agent of any kind. The medical skin application agent in particular preferably has at least one transdermal active ingredient.

The skin application agent is preferably a skin cleansing agent, preferably a washing paste and particularly a hand washing paste. These skin cleansing agents can contain organic solvents in addition to the polyisoprene latex.

The solvent preferably has a lower volatility than ethanol and a boiling point >78.32° C., the boiling point being measured at a pressure of 1.013 bar. The solvent preferably is at least one polyhydric alcohol or derivative of a polyhydric alcohol, particularly a polydiol, preferably an alkylene glycol, a polyalkylene glycol, a polydiol derivative, and preferably a polyalkylene glycol ether and/or polyalkylene glycol ester, mono- or polyester of a saturated or unsaturated mono- or polyvalent carboxylic acid with 2 to 30 carbon atoms with n- and isoalkanols with 2 to 10 carbon atoms, preferably a diester of aliphatic and/or aromatic di- and/or tricarboxylic acids, and/or aliphatic hydrocarbon with 12 to 22 carbon atoms, preferably with 16 to 20 carbon atoms and particularly preferably isohexadecane, or a mixture of at least two of the above-mentioned substances.

Preferred polyalkylene glycols or their esters or ethers are listed in the tables from Ullmann, 4th edition, volume 8, pages 200, 204, 205, 207 and volume 19, pages 426 and 428.

These tables are hereby incorporated by reference and are thus deemed part of the disclosure.

Particularly preferred is the solvent dipropylene glycol monomethyl ether.

The ratio of polyisoprene latex to solvent is preferably 8:1 to 1:1, and more preferably 4:1 to 2:1.

The skin cleansing agent may optionally contain a surfactant. This surfactant is preferably a fatty alcohol ethoxylate of general formula: $R-O-(CH_2-CH_2-O)_n$ with $R=C_{8-18}$ and $n=1-8$, preferably $R=C_{12-14}$ and $n=4-6$. The surfactant is also preferably a fatty alcohol ether sulfate of general formula: $R-O-(CH_2-CH_2-O)_n SO_4 X_2$ with $R=C_{10-16}$ and $n=1-4$ and $X=Na^+, K^+, ½ Mg^{2+}$ or $NH_4^+$.

The skin cleansing agent preferably contains at least one abrasive. The abrasives can be conventional abrasives or mixtures thereof, and preferably bleached walnut shell meal, non-swellable starch or a mixture thereof.

To modify the consistency of the skin cleansing agent, the latter can also contain water-swellable polymers as thickeners, whereby polymers obtainable from the polymerization of acrylic acid and xanthan gum are preferably employed.

The skin cleansing agent may contain cosmetic adjuvants and/or additives and/or active ingredients, e.g. care derivatives, emollients, perfume (fragrances), preservatives etc..

In a preferred embodiment, the skin cleansing agent contains:

a) 10–80% by weight of a liquid natural and/or synthetic water-based polyisoprene latex emulsion, b) 1–15% by weight of an organic solvent having a lower volatility than ethanol and a boiling point >78.32° C., c) 0–10% by weight of at least one surfactant, preferably at least one fatty alcohol ethoxylate, fatty alcohol ether sulphate, succinate, sarcoside and/or glucoside, d) 0–10% by weight of abrasives, preferably bleached walnut shell meal and/or non-swellable starch, e) 0–1% by weight thickener, f) optionally cosmetic adjuvants and additives and/or active ingredients, g) 10–60% by weight water, to make a total of 100% by weight.

In another preferred embodiment, the skin application agent is a face mask which preferably contains 60–80% by weight polyisoprene and 20–40% by weight water and possibly 0–20% by weight additives, the total always yielding 100% by weight.

The additives are preferably cleansing and/or care components. Examples of cleansing components are ionic and nonionic surfactants, preferably wheat germ hydrolyzates, betaines, sarcosides and/or sulfosuccinates.

Preferably employed as the care components are at least one vitamin, at least one herb or at least one component of a herb, at least one herbal mixture, e.g. bisabolol, azulene, at least one fruit powder and/or at least one component of a fruit, particularly a vitamin, a fruit powder and, for instance, bisabolol, azulene and/or panthenol-2 and/or tanning components, e.g. hamamelis.

In another preferred embodiment of the present invention, the skin application agent is a plaster, and particularly a spray plaster.

The advantage of the skin application agent according to the invention is that it is toxicologically safe and less harmful to the environment and irritates the skin at least no more than products of the prior art.

The present invention is also directed to a method for the medical and/or cosmetic treatment of the skin, characterized in that a skin application agent according to the invention is applied to the skin, left there for a certain period and removed subsequently or immediately after application, being preferably rubbed off and/or washed off.

The time for which the skin application agent according to the invention is left on the skin depends on the agent's purpose. For a hand washing paste the period is 1 to 2 minutes, for a face mask 10 to 30 minutes, and for a plaster several days. The person skilled in the art realizes that, in the case of a plaster and particularly a spray plaster, the skin application agent according to the invention can also be removed together with the slough.

The advantage of the method according to the invention is that it is toxicologically safe and less harmful to the environment.

The invention will be explained below with reference to the Examples. These explanations merely exemplify and do not limit the general idea of the invention.

A. Hand Washing Pastes

Test Methods

1. Skin Compatibility, Using the Duhring Chamber Test

This method is an in vivo test model for examining the skin compatibility of various test products in a direct comparison. The products being tested are applied in air-permeable aluminum chambers (18 mm diameter Finn Chambers®) each time to the same test area on the volar side of the lower arms of 20 test subjects on four successive days. The application times are two hours on the first, four hours on the second and six hours on the third and fourth days respectively. The Finn Chambers® are fastened with strips of adhesive plaster. In the event of strong dermal effects, the test is discontinued for each test field before the completion of the overall application time. The skin irritations produced are assessed according to the scale given below and the application times.

R=Reddening (erythema): 0=no erythema, 4=pronounced erythema

P=Peeling: 0=no peeling, 4=pronounced peeling

F=Fissures: 0=no fissures, 4=pronounced fissures

The resultant assessment criteria are a) Irritation as the mean of the sum of irritation values of R, P and F of n test subjects;

b) Application time as the mean of the tolerated application times in hours of n test subjects.

2. Testing Cleansing Performance

Two products are tested in a comparison on at least eight test subjects. Essential for this is that the palms of the hands of all test subjects have a skin structure typically attributable to manual labour. The following test is carried out in the morning and afternoon with one product in each case:

A defined quantity of model dirt (0.2 to 0.5 g) is spread onto the palm and back of the hand and rubbed for 45 s.

It is left to dry for 1½ min.

A defined quantity of the test product (0.3 to 1.8 g) is applied and rubbed in.

After slight drying, the product is removed with the absorbed dirt by rubbing.

Visual assessment of the residual soiling (RS) on the back and palm of the hand in accordance with the scale (see below).

0=clean; 5=no cleansing effect (0.5 gradations are possible)

$RS_{palm}$=mean residual soiling of the palm of the hand from n series of measurements (test subjects)

$RS_{back}$=mean residual soiling of the back of the hand from n series of measurements (test subjects)

Composition of a model dirt suitable for the test:

| Motor oil | 54.15% |
|---|---|
| Vaseline | 18.05% |
| Adeps lanae | 18.05% |
| Graphite | 3.61% |
| Flame soot | 5.42% |
| Iron oxide ($Fe_2O_3$) | 0.72% |

3. Toxicological Test

The toxicological evaluation of the natural and/or synthetic water-based latex emulsion can be ascertained by determining cytotoxity and by employing the neutral red test.

The test is carried out in accordance with European Standard EN 30 993-5, whereby, with omission of the 72 h incubation period, the test substance is diluted in the cell culture medium and applied to the cells.

The latex emulsion employed was a polyisoprene latex with the designation KRATON® IR-RP 401 from Shell AG.

| Cells | Balb/c 3T3 | Vehicle | DMEM |
|---|---|---|---|
| Dilution | 10% (w/v) | pH | 8.22 |

Neutral Red Uptake

| Concentration (mg/ml) of test substance | 0 | 1 | 2.5 | 5 | 7.5 | 10 | 25 | 50 | 100 |
|---|---|---|---|---|---|---|---|---|---|
| Inhibition (%) of neutral red uptake | | −5.89 | −8.70 | 15.07 | 38.44 | 57.74 | 72.22 | 80.31 | 82.42 |

$NR_{50}$ value:

PT: 7.0 mg/ml (preliminary test)

T: 9.0 mg/ml (test)

Assessment

The tests yield $NR_{50}$ values of 7.0 mg/ml and 9.0 mg/ml respectively. The product can therefore be classified as weakly cytotoxic.

EXAMPLE

To test cleansing performance and skin compatibility, 9 hand washing pastes were produced, the compositions of which can be seen in the following Table 1, with the data given in % by weight.

TABLE 1

| | Example | | | | | | | |
|---|---|---|---|---|---|---|---|---|
| | 1 | 2 | 3 | 5 | 6 | 7 | 8 | 9 |
| Kraton IR 401 latex | 17 | 30 | 50 | 80 | 80 | 30 | 30 | 30 |
| PPG-2 methyl ether | 15 | 10 | 5 | 10 | 5 | | | |
| Di-n-butyl adipate | | | | | | | 10 | |

TABLE 1-continued

| | Example | | | | | | | |
|---|---|---|---|---|---|---|---|---|
| | 1 | 2 | 3 | 5 | 6 | 7 | 8 | 9 |
| PEG 4 | | | | | | | 10 | |
| Hexylene glycol | | | | | | | | 10 |
| Iso-hexadecane | | | | | | | | |
| Pareth-5 | | 3 | 3 | 3 | | 3 | 3 | 3 |
| Laureth-6 | 1 | | | | 3 | | | |
| Water | 60 | 50 | 35 | 0 | 5 | 50 | 50 | 50 |
| Walnut shell meal | 6 | 6 | 6 | 6 | 6 | 6 | 6 | 6 |
| Thickener | 1 | 1 | 1 | 1 | 1 | 1 | 1 | 1 |
| Total | 100 | 100 | 100 | 100 | 100 | 100 | 100 | 100 |

TABLE 2

| | | | | | | | | |
|---|---|---|---|---|---|---|---|---|
| Skin compatibility | 0 | 0 | + | 0 | + | + | + | + |
| Skin cleansing compared to Castrol Super Clean | + | + | 0 | + | 0 | + | 0 | 0 |

Kraton® IR 401 latex=isoprene latex from Shell Chemicals UT Ltd.

PPG-2 methyl ether=dipropylene glycol monomethyl ether

PEG 4=polyethylene glycol 400 P

Pareth-5=polyethylene glycol ether of a mixture of synthetic $C_a$–$C_{11}$ fatty alcohol (n=5)

Laureth-6=lauryl alcohol polyethylene glycol ether (N=6)

Thickener=Carbopol ETD 2020: acrylic acid copolymer (98–100%)

All the substances given in Table 1 were toxicologically assessed and classified ed as unproblematical.

The hand washing pastes given as Examples 1–9 were compared to Castrol Super Clean, a Castrol Ltd. product. The results of the comparison are summarized in Table 2, whereby 0 indicates "comparable" and + "superior".

B. Face Masks
  A: Chamomile car e mask
  B: Cleansing mask
  C: Astringent/tanning mask
  D: Care/tanning mask
  E: Toning mask

| | A | B | C | D | E |
|---|---|---|---|---|---|
| Kraton IR | 40 | 40 | 40 | 40 | 40 |
| Laureth-5 | 5 | 5 | 5 | 5 | 5 |
| Water | 53.18 | 38.4 | 49.4 | 49.08 | 38.4 |
| Xanthan Gum | 0.6 | 0.6 | 0.6 | 0.6 | 0.6 |
| α-Bisabolol | 0.3 | | | 0.3 | |
| Azulene | 0.02 | | | 0.02 | |
| Panthenol-L | 0.9 | | | | |
| Kaolin | | 5 | | | |
| Rice starch | | 10 | | | |
| Silicic acid | | 1 | | | 1 |
| Extrapon hamamelis extract | | | 5 | 5 | |
| Alcohol | | | | | 10 |
| Herbal mixture | | | | | 5 |

What is claimed is:

1. A skin application agent selected from the group consisting of a washing paste, a plaster and a face mask, containing a polyisoprene latex, wherein the polyisoprene has a content of cis-1,4-isoprene of at least 90% by weight.

2. The skin application agent according to claim 1, wherein the particle size in the latex is 1.8 µm at maximum.

3. The skin application agent according to claim 1, wherein the polyisoprene latex is water-based and has 20–90% by weight solids.

4. The skin application agent according to claim 1, wherein the polyisoprene latex is water-based and has 60–80% by weight solids.

5. The skin application agent according to claim 1, which is a skin cleansing agent in the form of a washing paste.

6. The skin application agent according to claim 5, also containing an organic solvent.

7. The skin application agent according to claim 6, wherein the solvent has a lower volatility than ethanol and a boiling point greater than 78.32° C., measured at a pressure of 1.013 bar.

8. The skin application agent according to claim 7, wherein the solvent is at least one selected from the group consisting of polyhydric alcohols, ethers of polyhydric alcohols, esters of polyhydric alcohols; mono- and polyesters of saturated or unsaturated mono- or polyvalent carboxylic acids having 2 to 30 carbon atoms with n- and isoalkanols having 2 to 10 carbon atoms; and aliphatic hydrocarbons having 12 to 22 carbon atoms.

9. The skin application agent according to claim 6, wherein the ratio of polyisoprene latex to solvent is 8:1 to 1:1.

10. The skin application agent according to claim 9, wherein the ratio is 4:1 to 2:1.

11. The skin application agent according to claim 6, wherein the solvent is dipropylene glycol monomethyl ether.

12. The skin application agent according to claim 5, which also contains a surfactant.

13. The skin application agent according to claim 12, wherein the surfactant is a fatty alcohol ethoxylate of formula: R—O—(CH$_2$—CH$_2$—O)$_n$H wherein R is $C_{8-18}$ and n is 1–8.

14. The skin application agent according to claim 13, wherein R is $C_{12-14}$ and n is 4–6.

15. The skin application agent according to claim 12, wherein the surfactant is a fatty alcohol ether sulphate of formula: R—O—(CH$_2$—CH$_2$—O)$_n$SO$_4$X$_2$ wherein is $C_{10-16}$, n is 1–4, and X is Na$^+$, K$^+$, ½ Mg$^{2+}$ or NH$_4^+$.

16. The skin application agent according to claim 5, which also contains at least one abrasive.

17. The skin application agent according to claim 5, which also contains thickening amounts of a water-swellable polymer.

18. The skin application agent according to claim 5, which additionally contains at least one of a cosmetic adjuvent, a cosmetic additive, and an active ingredient.

19. A skin cleansing agent comprising:
  a) 10–80% by weight of a liquid natural and/or synthetic water-based polyisoprene latex emulsion, wherein the polyisoprene has a content of cis-1,4-isoprene of at least 90% by weight.
  b) 1–15% by weight of an organic solvent having a lower volatility than ethanol and a boiling point >78.32° C.,
  c) 0–10% by weight of at least one surfactant,
  d) 0–10% by weight of an abrasive,
  e) 0–1% by weight thickener,
  f) optionally cosmetic adjuvants and additives and/or active ingredients,
  g) 10–60% by weight water, to make a total of 100% by weight.

20. The skin cleansing agent according to claim 19, wherein the surfactant is at least one fatty alcohol ethoxylate, fatty alcohol ether sulphate, succinate, sarcoside, glucoside, or mixtures thereof.

21. The skin cleansing agent according to claim 19, wherein the abrasive is bleached walnut shell meal, non-swellable starch, or a mixture thereof.

22. A skin application agent in the form of a face mask which comprises 60–80% by weight of polyisoprene and 20–40% by weight water.

23. The skin application agent according to claim 22, which also contains cleansing and/or care components.

24. The skin application agent according to claim 23, wherein the cleansing component is at least one ionic or nonionic surfactant.

25. The skin application agent according to claim 24, wherein the surfactant is at least one of wheat germ hydrolyzate, betaine, sarcoside, and sulfosuccinate.

26. The skin application agent according to claim 22, which also contains fat absorbing amounts of at least one of kaolin, starch, and starch derivatives.

27. The skin application agent according to claim 23, wherein the care component is at least one selected from the group consisting of vitamins, herbs, components of herbs, herbal mixtures, fruit powders, components of fruits, and tanning components.

28. The skin application agent according to claim 1, which is in the form of a plaster.

29. The skin application agent according to claim 28, wherein the plaster is a spray plaster.

30. A method for the medical and/or cosmetic treatment of the skin comprising applying the skin application agent of claim 1 to the skin for a time sufficient to provide medical and/or cosmetic treatment, and then removing said skin application agent.

31. The method according to claim 30, wherein the skin application agent is removed immediately after application.

32. The method according to claim 30, wherein the skin application agent is removed by rubbing off.

33. The method according to claim 30, wherein the skin application agent is removed by washing off.

* * * * *